(12) United States Patent
Ball (10) Patent No.: US 7,234,467 B2
(45) Date of Patent: Jun. 26, 2007

(54) OCCLUSAL SPLINT

(75) Inventor: Harry Ball, Elsternwick (AU)

(73) Assignee: Myohealth IP Pty Ltd, Brighton East (AU)

( * ) Notice: Subject to any disclaimer, the term of this patent is extended or adjusted under 35 U.S.C. 154(b) by 0 days.

(21) Appl. No.: 10/835,649

(22) Filed: Apr. 30, 2004

(65) Prior Publication Data

US 2005/0022824 A1 Feb. 3, 2005

(30) Foreign Application Priority Data

Jul. 25, 2003 (AU) ............... 2003903900

(51) Int. Cl.
*A61F 5/56* (2006.01)
(52) U.S. Cl. .................................. 128/848
(58) Field of Classification Search ........... 128/848, 128/859, 861; 433/1, 6
See application file for complete search history.

(56) References Cited

U.S. PATENT DOCUMENTS

| | | | |
|---|---|---|---|
| 3,813,781 A * | 6/1974 | Forgione | 433/68 |
| 4,169,473 A * | 10/1979 | Samelson | 128/848 |
| 4,504,225 A * | 3/1985 | Yoshii | 433/6 |
| 5,513,656 A | 5/1996 | Boyd, Sr. | |
| 5,795,150 A | 8/1998 | Boyd | |
| 5,876,199 A * | 3/1999 | Bergersen | 433/6 |
| 6,071,121 A | 6/2000 | Simon | |
| 6,231,337 B1 | 5/2001 | Boyd | |
| 2003/0116164 A1 | 6/2003 | Boyd, Sr. | |

FOREIGN PATENT DOCUMENTS

WO  WO 96/29950    10/1996
WO  WO 03/051280 A2  6/2003

* cited by examiner

*Primary Examiner*—Henry Bennett
*Assistant Examiner*—Camtu Nguyen
(74) *Attorney, Agent, or Firm*—Pearne & Gordon LLP (57) ABSTRACT

The present invention is directed to an improved form of a splint having a contact portion for maintaining the vertical separation of rearwardly opposed teeth in the oral cavity of a patient wearing the splint. The splint is provided with a contact portion for contacting opposed forward teeth to the forward teeth to which the splint is attached such that movement of the opposed forward teeth with respect to the contact portion maintains the spacing of the rearward teeth. The contact portion is provided with a central or intermediate section to which a forward portion is angularly inclined. The splint is optionally provided with a third portion angularly inclined to the central or intermediate portion for stabilising the position of the jaw or teeth to prevent permanent or long term change in the jaw position (strictly).

34 Claims, 5 Drawing Sheets

OCCLUSAL SPLINT

The present invention relates generally to intra-oral devices, and in particular to improvements in or to new forms of intra-oral devices. In particular, some embodiments of the present invention relate to intra-oral devices of the type that are worn by patients suffering from certain conditions which occur during sleep, such as for example, conditions associated with sleep disorders, bruxism or the like, in which the devices are provided with a contact portion for contact by opposing teeth in order to prevent a patient's rearwardly located teeth from contacting each other. Even more particularly, some embodiments of the present invention relate to an occlusal device having a modified contact portion and to methods of using such device, for inhibiting the forces of bruxism, and hence reducing or eliminating potential damage to teeth, including restored or repaired teeth or similar, caused as a result of voluntary or involuntary jaw clenching and grinding which usually occurs whilst the person is asleep. However, such conditions can occur during the day also.

The present invention finds particular application as an occlusal splint having a modified contact portion and a method of using such an occlusal splint, in which the modified contact portion facilitates improved contact between the splint, particularly the contact portion of the splint, and the opposed forwardly located teeth (anterior teeth) in order to prevent opposed more rearwardly located teeth (posterior teeth) from contacting each other during use, particularly from contacting each other in a grinding movement. A particularly preferred form of the occlusal device of the present invention has an improved or modified contact portion which comprises two or more clearly defined contact surfaces, areas or portions which are substantially angularly inclined to each other so as to control movement of the teeth when the jaw moves in order to maintain the rearwardly opposed teeth in spaced apart relationship to each other during use, and in some instances to increase the distance that the teeth are in spaced apart relationship to each other, particularly the vertical spacing of the teeth. Thus, the splint is designed to stay in place on the front teeth to prevent the rear teeth from touching each other.

Although the present invention will be described with particular reference to one form of an occlusal device having a compound contact portion in the form of a ramp or similar comprising at least two angularly inclined parts or surfaces for keeping opposed rearwardly located teeth in spaced apart relationship from each other during use, it is to be noted that the scope of the present invention is not restricted to the described embodiment, but rather the scope of the present invention is more extensive so as to include other forms and arrangements of the intra-oral device, other forms and arrangements of the contact portion, including different arrangements and orientations of the respective parts or portions of the contact surface, and the use of the various different forms of the device in a wide variety of situations for treating numerous conditions and disorders amongst a wide range of patients having different mouth types, mouth anatomy or the like.

The habit of clenching the jaw and jaw muscles to bring the upper and lower teeth together and moving the teeth against each other particularly moving the teeth laterally against one other, is a problem or condition suffered by a significant number of the population. The general description of such movements of the jaw is bruxism. Normally, bruxism has two components which are (i) clenching of the jaw to force the teeth together against each other whilst maintaining the teeth static and (ii) grinding of the teeth which involves moving the teeth laterally against each other. Bruxism encompasses either one or both of these movements so that patients can suffer from a variety of forms of bruxism.

Bruxism which includes any combination of clenching and/or grinding of the teeth can present serious dental health problems as well as produce general health problems. The term "bruxism" is more accurately defined as "the parafunctional clenching and grinding of teeth". If left untreated, bruxism can lead to attrition and damage of tooth surfaces, loss of vertical dimension of occlusion, increased muscle tone, or tension or strains, fracture of teeth, chipping of teeth and pathological changes in the temporo mandibular joints (TMJs). It can also lead to muscle or muscular disease or dysfunction within muscles, such as for example, pathological changes within the muscles, typically in the masticatory muscles. The damage to masticatory muscles or structures is related to the duration and magnitude of force applied during the parafunctional activity. The greater the force, the greater the damage.

Such grinding and clenching of the teeth is often associated with stress, and although bruxism can occur during the day or at night whilst the patient is asleep the forces of bruxism are greater at night and accordingly, more damage occurs at night. Often the patient is unaware of this condition and of the harm that is being caused until the damage is manifest and/or observable. It is often only when the harm or damage becomes apparent that the condition is diagnosed which is often too late to effect a complete cure or rehabilitation since amelioration of the condition often requires expensive and extensive treatment. Grinding of the teeth results from a patient tightly clenching his or her jaw muscles, thereby forcing together the occlusal surfaces of the opposed upper and lower teeth, sometimes with considerable force. As well as the actual clenching action itself, in which the opposed teeth are brought into contact with each other, the jaw muscles cause the upper and lower teeth to move laterally with respect to each other simultaneously while being forced into contact with each other, hence producing a grinding action in the teeth. Such grinding can, if unchecked, result in serious damage to the teeth of the patient, as well as compounding the harm caused by the clenching action. The damage also includes damage to teeth that have previously being restored and/or repaired, such as for example, fillings, crowns or the like. As an example, in the short term, constant grinding can wear enamel from tooth surfaces, particularly the crown or cusp of the tooth. In the long term, grinding can eventually wear through the enamel of the tooth and into the tooth pulp itself and/or through any previous repairs or restorations to or of the teeth, leading to irrepairable damage and harm to the tooth and nerves, such as for example, causing fractures of teeth or the like, as well as requiring further expensive restorations. Furthermore, the dysfunction of the clenching muscles, when chronic, can lead to the development of conditions such as temporo mandibular disorders, tension-type headaches, migraine and the like, resulting in permanent and/or temporary harm and/or injury to the patient.

Although there have been a number of different appliances or devices for treating bruxism in the past, including devices known as occlusal devices, splints or the like all of the previously available devices have suffered from one or other defect or shortcoming when used to ameliorate the effects of bruxism. One form of the splints currently available termed "flat plane full mouth splints" are relatively large in size and accordingly, are uncomfortable to wear, particularly for lengthy periods of time, such as for example during sleep. Usually, such splints are so uncomfortable that many patients do not persist with their use and end up not wearing them thereby negating any benefit that may be derived from their use. Other types of splints which contact the front two incisor teeth only are smaller in size and hence more comfortable to wear but have a tendency to be dislodged easily from the teeth since they are held in contact with two teeth only, usually the upper pair of central incisors. Owing to their small size there is insufficient area of contact between the splint and the teeth to securely hold the splint in place during use. Also again owing to their small size, when the device dislodges from contact with the teeth there is a risk that such devices may be swallowed or inhaled, particularly when the fit between the device and the teeth becomes loose after prolonged use and wear.

Other devices are provided with a contact portion to assist in maintaining the posterior teeth in spaced apart relationship to each other in which the contact position is in the form of a dome or ramp or similar protrusion or projection which usually extends beyond the front surface or face of the splint. However, in some embodiments of splints having a contact portion the size or area of the contact projection is insufficient to maintain the posterior teeth in spaced apart relationship as there is a tendency for the opposed front teeth to slide off the contact portion allowing the rear teeth to contact one another as the contact portion keeping the teeth apart is no longer positioned in the correct place to achieve this. Additionally, the shape of the contact surface being planar allows relative movement of the upper and lower arches containing the upper and lower teeth, respectively, with respect to one another so that it is still possible for the rear teeth to grind against one another even if the front teeth are in contact with the splint. Whilst such prior art splints are effective to an extent, there is the real possibility that the rear teeth could come into contact with each other even when the device is being worn owing to the size and shape of the contact portion. Whilst such devices go some way towards alleviating the effects of bruxism, they still suffered from a number of problems or disadvantages. One problem of existing contact portions is that in order for the contact portion to work successfully to take advantage of the jaw opening reflex, which is a reflex action activated by the incisor teeth being clenched, the contact portion needed to be so large or to intrude into the mouth to such an extent to ensure that the incisor teeth contacted the contact portion before the rear teeth came into contact with each other, that the splint was uncomfortable to wear. If the contact portion was made small there was provided only minimal separation of the opposed rear teeth.

As a consequence, there is a need for an occlusal splint which is comfortable to wear, yet provides sufficient spacing between the opposed rear teeth to inhibit bruxism so as to eliminate or reduce the adverse effects caused by bruxism, and which controls or guides movement of the jaw, particularly the lower jaw or mandible to a greater extent in order to prevent or reduce the amount of contact between the rearwardly located teeth.

Therefore, it is an aim of at least some embodiments of the present invention to provide an occlusal splint which is comfortable to wear by being small in size, typically smaller in size than the flat plane full mouth splints.

It is another aim of at least some other embodiments of the present invention to provide an occlusal splint that suppresses the intensity of the forces of bruxism.

It is a further aim of at least some other embodiments to provide an occlusal splint that reduces the vertical dimensions of separation between opposed teeth whilst still maintaining the teeth in spaced apart relationship to each other.

It is a further aim to provide an occlusal splint that produces less strain on the Temporo-mandibular joint (TMJ).

It is a further aim of the present invention to provide a splint which provides sufficient separation for the opposed rear teeth from one another, and which controls the movement of the opposed front teeth so as to maintain the gap between the opposed rear teeth.

It is a further aim to provide a splint with a compound contact portion that has at least two contact surfaces located in two different planes.

According to one aspect of the present invention there is provided an occlusal splint for suppression of the intensity of forces of bruxism resulting from grinding and/or clenching of teeth of a person suffering from bruxism, said device comprising a body portion having a retaining means for securing the splint to at least some of the forward teeth of one arch of teeth of a person suffering from bruxism in order to locate the splint in a predetermined position in the mouth of the person, the body portion being provided with a contact portion arranged to face in a direction towards at least one of the front teeth of the other arch of teeth of the person, said front teeth of the first arch being opposed to the front teeth of the second arch when the splint is located in place in the mouth, wherein the contact portion includes at least a first portion or section for receiving the opposed forward teeth of the second arch when the teeth are in the normal habitual teeth together position during the use of the splint and a second section which is located adjacent the first section for guiding movement of the opposed front teeth of the second arch when the jaw is clenched so that when the teeth are in the normal habitual teeth together position at least one of the opposed forward teeth of the second arch contacts the contact portion so as to at least maintain spacing of at least some the rearwardly located teeth of one arch in spaced relationship from at least one of the rearwardly located teeth of the second arch and when the jaw is clenched at least one of the opposed forward teeth of the second arch is guided from the normal habitual teeth together position by movement along or with respect to the second section so as to at least maintain spacing of the rear opposed teeth of the first and second arch thereby preventing the opposed rear teeth from touching each other so as to suppress the intensity of forces of bruxism.

Typically, the retaining means is a cavity, chamber, pocket, groove, slot, opening or similar located at or towards one end of the occlusal splint. More typically the retaining means is located along the upper surface in use of the splint. Even more typically the retaining means is shaped so as to receive one or more of the front teeth. Even more typically the retaining means is shaped so as to receive the front teeth of the upper arch of teeth of the person wearing the splint. Even more typically, the retaining means receives at least two upper front teeth, preferably two or more upper front teeth, more preferably 4 to 6 upper front teeth, and most preferably six upper front teeth. Even more typically, the retaining means of the splint is molded to be received by and held in place by the six central or anterior or front upper teeth.

Typically, the splint of the present invention maintains the minimal separation of the opposed rearwardly located teeth from one another. More typically, the separation between the opposed rearward teeth becomes greater as the opposed forward teeth move forward with respect to each other.

Typically, bruxism may occur during the day or at night, and the effects of reduced bruxism using the splint of the present invention occur whilst the device is being worn, typically at night. More typically, there is research to suggest that when the device is worn there is up to about 70% reduction in the intensity of force of bruxism.

Typically, the normal habitual teeth together position includes a teeth contact position that corresponds to the centric occlusion position when the mouth is empty of devices.

Typically, movement of the forwardly located teeth with respect to the splint, preferably with respect to the contact portion of the splint, is in a generally forward direction and optionally in a sideways direction or in both directions.

Typically, the splint cooperatively engages with at least four or more front teeth, more typically, with at least five or more front teeth, and preferably at least six front teeth. However, the splint can be fitted to 8 10 or even 12 upper teeth. Typically, the splint is retained on the central upper teeth, such as the incisior teeth.

Typically, the front teeth are anterior teeth. More typically, the anterior teeth are the two pairs of incisor teeth and the first pair of canine teeth located on either side of the incisor teeth. Although the splint can be fitted to the upper or lower teeth, it is preferred that the splint is fitted to the upper teeth so that the lower teeth are the opposed teeth. When fitted to the upper teeth, the contact surfaces face the lower front teeth and assist in controlling movement of the lower front teeth and/or lower jaw (mandible) to some extent so as to maintain spacing of the upper and lower rear teeth from each other.

Typically, the rearward teeth are posterior teeth, such as molars, including the first, second and third molars, and/or premolars, such as the first and second premolars and the like.

Typically, the contact portion has at least two contact parts, sections, portions, surfaces or the like. More typically, each of the contact surfaces is flat, linear, planar, smooth, continuous, tapered or the like. Alternatively, the contact surface or surfaces is or are curved, including surfaces that are concave, convex or the like.

Even more typically, at least one of the contact surfaces is an oblique plane, an inclined plane, a tapered plane. Even more typically, one of the two contact surfaces is flat or the like. Even more typically, the two contact surfaces of the splint are located in different planes to each other, more typically the two planes are inclined to each other, and even more typically the planes are substantially angularly inclined with respect to each other. Typically, the angle of inclination is from about greater than 90° to from about less than about 180°, preferably from about 110° to about 160°, and more preferably from about 115° to 145°.

Even more typically, the angle of inclination varies over the length of the contact portion so that the contact portion is substantially curved. Thus, the inclined portion can be flat or can be curved.

Typically, the curved portion can be convex or it can be concave, preferably concave to assist in maintaining the rearward teeth in spaced apart relationship.

Typically, the curved portion is slightly curved. More typically, the curve can be parabolic, circular, or other curved geometric shape or similar. Furthermore the curved portion can be of any diameter, curvature, size or the like.

Typically, the second portion of the contact portion is located forwardly of the first portion. Alternatively, the second portion is located rearwardly of the first portion.

Preferably, the contact portion includes a third section, surface or portion. Typically the third portion is located at the other side or end of the first section than the end having the second section. More typically the third portion is located more rearwardly of the other two portions. More typically, the first section is a central or intermediate portion and the second section is located more forwardly of the central section, and the third section is located more rearwardly or linearly or posteriorly so as to extend rearwardly of the device.

Typically, the third portion is a lip, shelf, ledge or similar. More typically, the lip is angularly inclined to the first or intermediate portion. Even more typically, the third section is tapered, preferably tapered in the opposite direction to the taper of the second section.

The forward portion is a forwardly inclined portion for increasing the clearance of the rearwardly located teeth, whereas the lip portion prevents substantial rearward movement of the lower jaw. Thus, the combination of the two sections controls movement of the teeth so as to maintain the spacing of the rearwardly located teeth. Typically, the third section stabilises or tends to stabilise the position of the teeth to or towards the usual habitual closing position.

Typically, the third or rearward portion is adapted to assist to at least maintain the spacing of the jaw and preferably, to increase the spacing of the jaw. Even more typically the rearward portion counters the tendency of the jaw to undergo a posterior shift forming a malocclusion. Even more typically, the third portion prevents posterior shift and assists in moving the jaw back into the normal position, particularly the normal habitual teeth together position. Even more typically, the device promotes centric occlusion whereby the top of the most rearward lower teeth and jaw are permitted to undergo substantially forward movement, preferably to the centre of the splint.

The present invention will now be described by way of non-limiting example, with reference to the accompanying drawings, in which.

With particular reference to FIGS. 4–9, there is shown one form of the occlusal splint of the present invention. This form of the occlusal splint, generally denoted as 2, is made from a plastics material and is moulded to the shape of the forward teeth of a patient so as to be adapted to receive the six centrally located forward teeth 40 of the upper arch of the mouth of a patient, such as for example, the two pairs of upper incisor teeth and the upper pair of canine teeth: The splint is formed with an upper part, generally denoted as 4, which has a plurality of, typically six pockets, indentations, recesses or the like 6 for receiving therein the centrally located forward upper teeth 40. Each pocket is for receiving one tooth so that the six teeth are collectively received in the six pockets. Pockets 6 or the like are one form of the retaining means of the present invention for retaining the splint in place in the mouth and accurately locate the splint in the mouth whilst also securing the splint to the teeth to retain the splint in the mouth. In use, each of the six upper forward teeth 40 referred to previously are received snugly in a respective one of moulded pockets 6. This ensures a good stable fit of the splint on the teeth so as to maintain the splint in the correct position on the teeth thereby preventing inadverent dislodgement into the oral cavity during use, such as when the patient is asleep thereby preventing the splint from being swallowed or inhaled.

The splint can be formed in a conventional manner, and is formed from conventional materials from which splints are made, such as suitable plastics materials or combinations of suitable plastics materials. In one embodiment, there is a relatively harder outer shell in the form of a tray or similar within which is located a layer of heat softenable material that is generally more readily shaped or moulded or the like than is the relatively harder outer material. To form the splint, and in some circumstances when adjustments to the splint are required the shell and inner layer are placed in hot water to soften the inner layer so as to make it mouldable, so that when the splint is placed in contact with the centrally located six upper teeth 40, the inner layer of the splint conforms exactly to the shape and profile of the six centrally located upper teeth 40 thereby forming the indentations 6. When the splint cools, the soft inner layer now moulded to the shape of the six upper central teeth hardens to retain this shape and the exact shape of the indentations of the teeth 6. In this manner, the splint 2 is held in place securely against the upper front teeth so that there is little or no tendency for the splint to be dislodged from the teeth, such as during use of the splint when the patent is asleep or similar and also to stabilise the splint against unwanted movement. The indentations for the teeth form the upper part 4 of the splint.

In another embodiment, the splint is made from a single material with the upper portion 4 adapted to be molded to the exact shape of the teeth 40.

Figure 1:
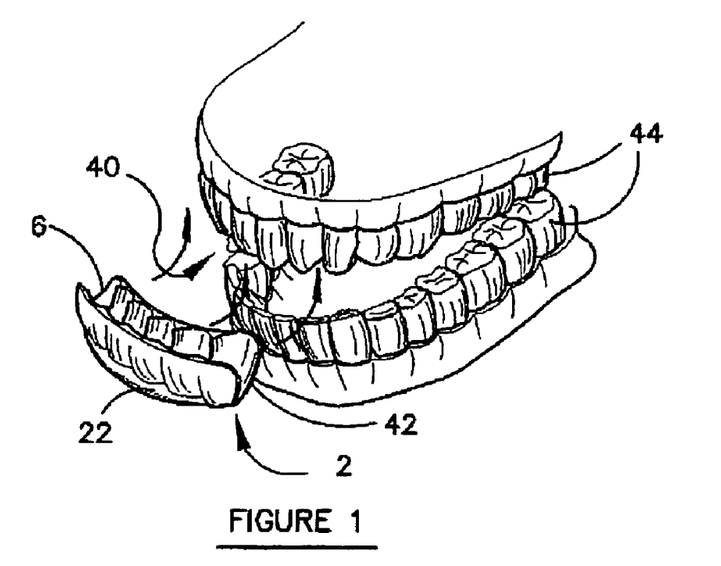
FIG. 1 is a front isometric view of the device preparatory to being placed against the forward teeth of the upper arch of the mouth.
Figure 2:
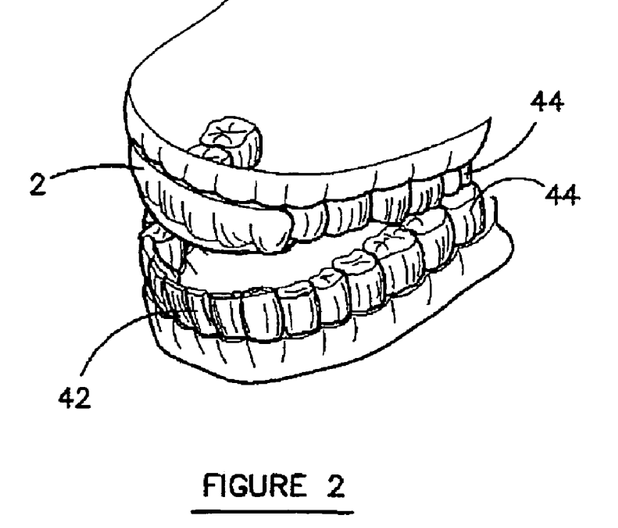
FIG. 2 is a front isometric view of the device in use in which the device is in contact with the upper front teeth of the mouth.
Figure 3:
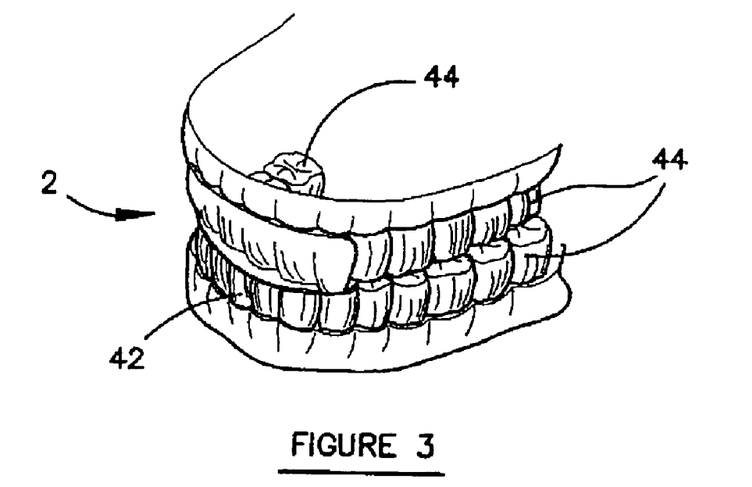
FIG. 3 is a front perspective view of the device in use when the person wearing the device is asleep with the mouth in the normal habitual mouth together position.
Figures 4, 5:
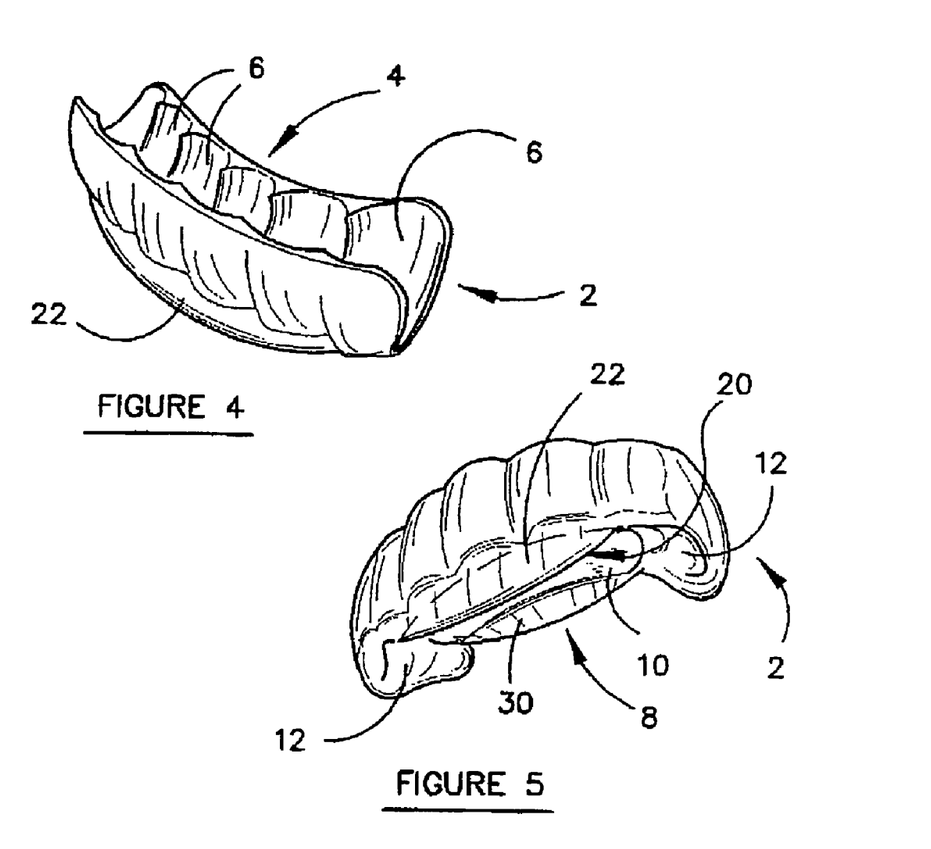
FIG. 4 is a front top isometric view of one form of the dental device of the present invention shown in isolation.
FIG. 5 is a front underneath view of the form of the device in FIG. 4 showing the angularly inclined surfaces forming the contact surface portion.
Figure 6:
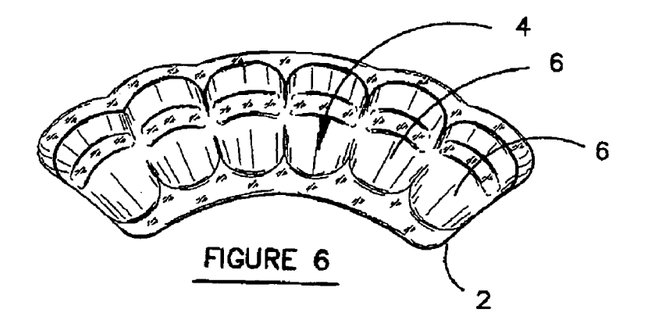
FIG. 6 is a top plan view of the form of the device in FIG. 4.
Figure 7:
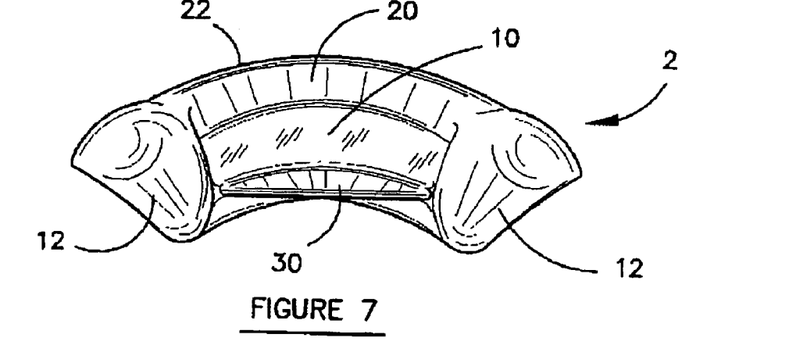
FIG. 7 is an underneath view of the embodiment shown in FIG. 4 showing the contact surfaces of the contact portion.
Figure 8:
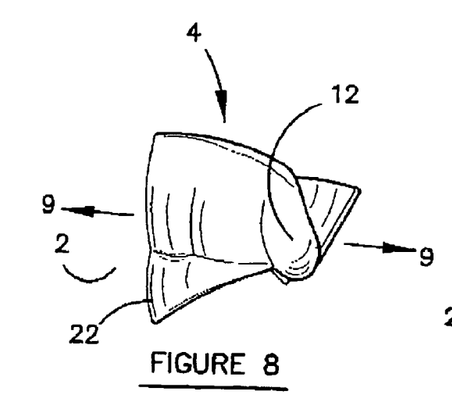
FIG. 8 is a one side elevation view of the embodiment of FIG. 4.
Figure 9:
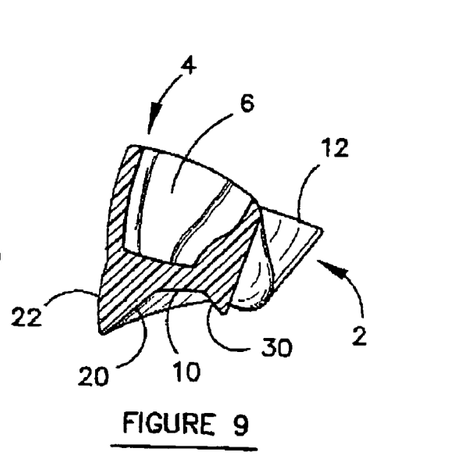
FIG. 9 is a cross-section of the device as shown in FIG. 8.
Figure 10:
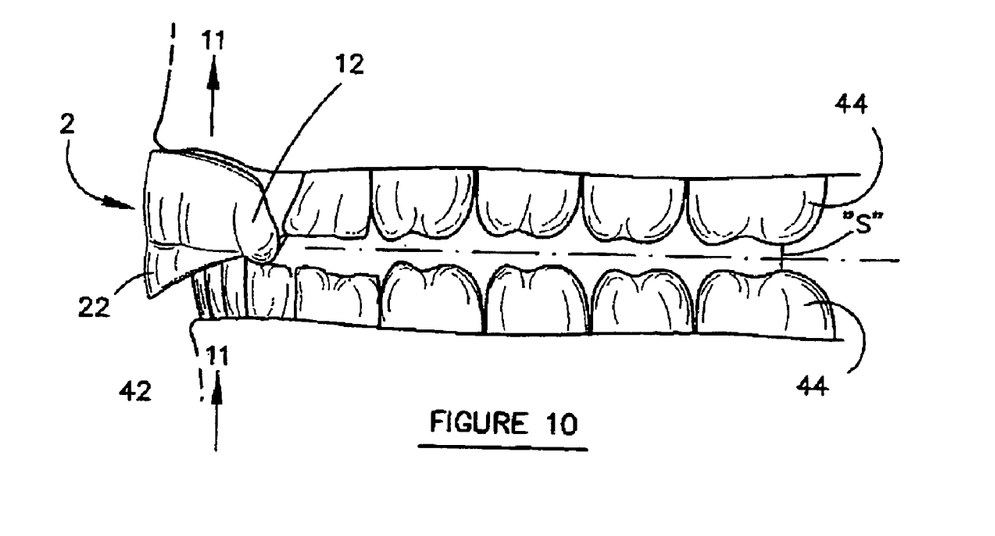
FIG. 10 is a side elevation view of the device in use in the usual habitual teeth together closing position when a person is asleep.
Figure 11:
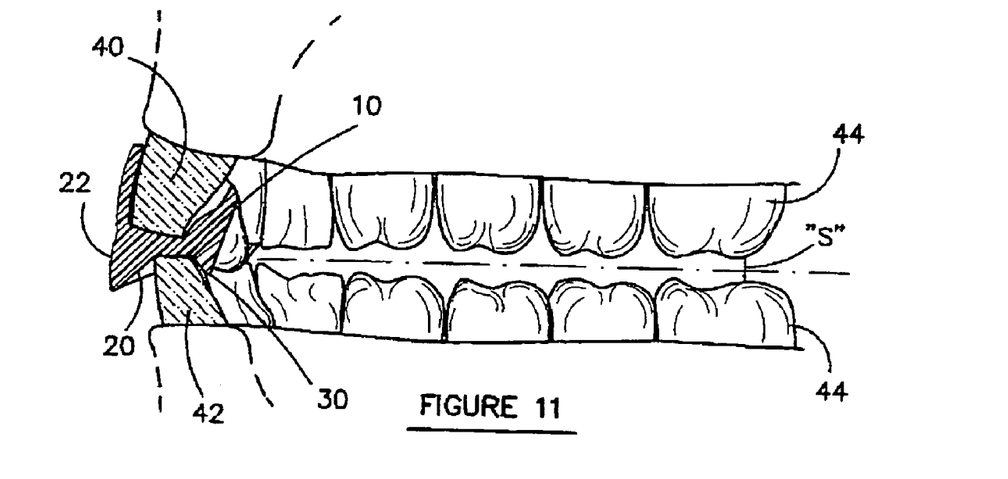
FIG. 11 is a sectional view along the line 11—11 of FIG. 10.

The underside of the splint, which is the part of the splint providing control for movement of the lower teeth or jaw, is provided with a cavity, groove, rebate, hollowed portion, or similar depression or the like. The cavity forms at least part of a contact portion, generally denoted as 8. The contact portion 8, in one embodiment, comprises three sections or portions 10,20,30, all of which are located in different planes from one another. One of the sections, which is referred to as the first section 10, is a flat or substantially flat section centrally located between the sides or ends 12 of the splint. Section 10 is a generally flat planar contact surface for contacting the lower front teeth 42 of the patient in use in the centric occlusion position or the normal habitual teeth together portion when they the teeth brux or clench. When the lower teeth 42 rest against this generally flat surface 10, the splint is generally comfortable to wear and yet maintains sufficient spacing "s" between the rearwardly located teeth 44, as shown more particularly in FIGS. 10 and 11, which illustrates the splint being worn in the normal habitual teeth together position which is comfortable as the spacing "s" is less than the spacing of previously available other splints when being worn by patients in an attempt to counter the effects of bruxism.

Figure 12:
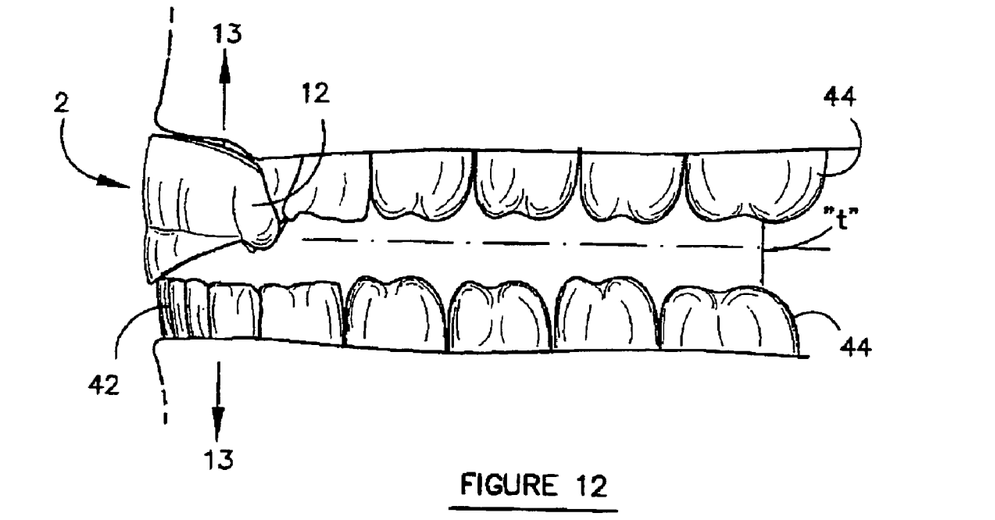
FIG. 12 is a side elevation view of the device in use when the lower jaw is in a more relatively forward position as a person moves their jaw, showing an increased spacing between the rear teeth.
Figure 13:
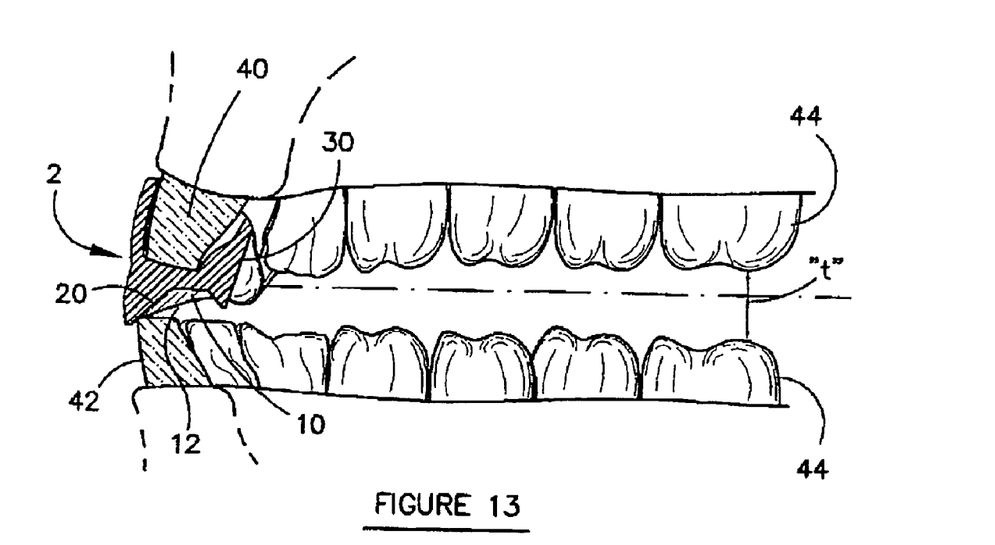
FIG. 13 is a cross-section view taken along the line 13—13 of FIG. 12.

The second section 20 of the contact portion 8 is located forwardly of central section 10 and takes the form of a generally forwardly inclined, tapered or sloping skirt 22 defining a generally tapered or inclined inner surface which is the contact surface for the upper edges of the centrally located lower teeth 42. The contact surface 20 extends in a plane that is substantially angularly inclined to the plane containing the flat central or intermediate surface 10. The tapering of the front or forward contact portion 20 is adapted so that when the lower jaw moves forwardly, the upper edges of the lower front teeth 42 contact the contact portion 20 so that the lower front teeth move along the inclined plane of this tapered forward to directed surface 20 to increase the spacing of the more rearwardly located teeth 44 to a spacing "t", which is greater than spacing "S" as shown particularly in FIGS. 12 and 13. Thus, any forward movement of the lower jaw either involuntarily or voluntarily results in the spacing of the rear teeth being least maintained substantially at a spacing "s" or more usually being increased substantially to a spacing "t" thereby overcoming the possibility of bruxism.

The more rearwardly located contact surface 30 is also an inclined, tapered or oblique contact surface in the form of a lip, ledge or similar. It is to be noted that the angle of inclination of the rear contact surface 30 is greater than that of contact section 20 but the length of contact section 30 is shorter than the length of section 20. Thus, the rear contact section 30 is steeper than contact portion 20. The lip 30 is angularly inclined to the centrally located flat contact surface 10, and is tapered in a direction opposite to the taper of the front contact portion 20. The intent or purpose of the lip is to prevent a permanent rearward movement or shift of the jaw which would have resulted in changes in the occlusion, or in other words, to maintain permanent stability of the jaw position.

It is to be noted that the extent of the general contact portion 8 is generally defined within the limits of the splint so that the front skirt 22, and more particularly front contact surface 20 does not extend beyond the front face of the splint and the rear contact surface 30 does not extend beyond the rear face of the splint. By the entire contact surface 8 being wholly contained with the boundary of the splint and not extending outwardly from the splint, the splint can be made more compact and is more comfortable to wear, particularly during sleep. Further, the splint 2 is made to extend generally arcuately about the mouth so as to be contoured to the curvature of the upper or lower arch within the mouth of the patient, preferably the upper arch. This promotes ease of use and comfort when in use as well as assisting in retaining the splint in place during use, such as when the patient is asleep.

Further, the sides 12 of the splint 2 are tapered to prevent unwanted sideways movement of the jaw when clenching.

In operation of the device 2 of the present invention, the splint allows the rearwardly located opposed teeth 44 to be more closely spaced towards each other, such as when in their centric occlusion habitual biting position, at a spacing "s", which is more comfortable for the wearer to use, particularly during long periods of sleep. However, any forward, or sideward movement of the jaw (immediate disclusion) is generally limited and contained by the sloping surfaces 20, 30 and sides 12 as well as by the contour and/or shape of the cavity. Additionally, the splint prevents rearward movement of the lower jaw. Thus, there is a tendency for the jaw and the occlusion to be stablised in the optimum position. In the event that there is forward or rearward movement of the jaw, the lower teeth move along the tapered contact surface of the front contact portion 20 or the rear contact portion 30 respectively, which increases the spacing between the rearward teeth, such as for example from a spacing "s" to a spacing "t" thereby preventing the rearward teeth from contacting each other as the spacing between the rear teeth is increased, preventing the teeth from grinding contact with each other as well as maintaining occulsal stability of the teeth and jaw in the long term.

Advantages of the present invention include that the occlusal splint is more comfortable to wear and owing to the angular inclination of the respective contact surfaces, the jaws tend to be maintained in this comfortable position. Any movement of the jaw, particularly the lower jaw, in any direction, increases the spacing of the rear teeth and there is a tendency for the jaw to return to the normal position and for the occlusion to remain stable in the long term even when the splint is not being worn.

The device of the present invention allows a clear gap "S" between opposed upper and lower rear teeth 44 initially. There is decreased vertical dimension and minimal vertical opening of the mouth which is more comfortable for the patient, and is less damaging to the muscles and TMJ. There is reduced strain on the jaw, muscles and the like and the reduced potential for joint muscular problems. The device allows lip seal during sleep which is desirable as it prevents inflamation of the gums, gum disease, peridontal disease from dry mouth conditions and other conditions caused by this, as well as preventing dry and/or cracked lips, mouth or the like which are usually present when similar devices are worn as such devices are large, which prevents the lips from closing and sealing. The contact portion does not extend extensively or excessively from the front of the device. More particularly, the device reduces, inhibits, prevents or the like permanent or long term posterior shift of the mandible and a change in the occlusion as a result of muscle deprogramming.

The described arrangement has been advanced by explanation and many modifications may be made without departing from the spirit and scope of the invention which includes every novel feature and novel combination of features herein disclosed.

Those skilled in the art will appreciate that the invention described herein is susceptible to variations and modifications other than those specifically described. It is understood that the invention includes all such variations and modifications which fall within the spirit and scope.

The claims defining the invention are as follows:

1. An occlusal splint for suppression of the intensity of forces of bruxism resulting from grinding and/or clenching of teeth of a person subjected to bruxism, said splint comprising a body portion having a retaining means for securing the splint to at least some of the forward teeth, including incisors but no molars, of a first arch of teeth of a person suffering from bruxism in order to locate the splint in a predetermined position in the mouth of the person, the body portion being provided with a contact portion arranged to face in a direction towards at least one of the front teeth of a second arch of teeth of the person, said contact portion permitting said second arch of teeth to move anteriorly, posteriorly or laterally relative to said first arch of teeth during use of said splint, said front teeth of the first arch being opposed to the front teeth of the second arch wherein the contact portion includes at least a first section for receiving the opposed forward teeth of the second arch when the teeth are in the normal habitual teeth together position during use of the splint, and a second section which is located adjacent the first section and which is angularly inclined to the first section for guiding movement of the opposed front teeth of the second arch when the jaw is clenched so that when the teeth are in the normal habitual teeth together position at least one of the opposed forward teeth of the second arch contacts at least part of the contact portion so as to at least maintain spacing of at least some of the rearwardly located teeth of said first arch in spaced relationship from at least one of the rearwardly located teeth of the second arch and when the jaw is clenched at least one of the opposed forward teeth of the second arch is guided from the normal habitual teeth together position by movement along or with respect to the second section of the contact portion so as to at least maintain spacing of the rear opposed teeth of the first and second arch thereby preventing the opposed rear teeth from touching each other so as to suppress the intensity of forces of bruxism.

2. A splint according to claim 1 in which the retaining means is a cavity, chamber, pocket, groove, slot indentation, or opening located at or towards one side or end of the splint for receiving at least some of the front teeth to maintain the splint in place in the mouth.

3. A splint according to claim 2 in which the retaining means comprises at least two indentations moulded to the shape of the teeth to be received in the indentations.

4. A splint according to claim 1 in which the contact portion allows for the spacing between the opposed rearward teeth being at least substantially maintained or substantially being increased as one or more of the opposed forward teeth move forward either along the first section and/or the second section of the contact portion.

5. A splint according to claim 1 in which the first set of teeth is the upper arch of teeth.

6. A splint according to claim 5 in which the teeth of the upper arch are the at least two upper central front teeth.

7. A splint according to claim 1 in which the first section of the contact portion is a central or intermediate portion and the second section of the contact portion is located adjacent or contiguous to the central section.

8. A splint according to claim 1 in which the contact portion further includes a third section in which the third section is located at or towards the other side or end of the first or central section than the side or end having the second section so that the first section is intermediate the second and third sections.

9. A splint according to claim 1 in which the second section of the contact portion is angularly inclined in a forward direction to the central or intermediate section so that movement of the second arch of teeth tends to increase the spacing of the rearwardly opposed teeth of the first and second arches of teeth.

10. A splint according to claim 1 in which the angle of inclination between the first section of the contact portion and the second section of the contact portion is from greater than about 90° to less than about 180°.

11. A splint according to claim 1 in which at least one or both of the contact sections forming the contact portion is curved, parabolic, circular or other curved geometric shape.

12. A splint according to claim 1 in which the third section is located more rearwardly of the first and second sections in which the first section is the central or intermediate section and the second section is the forward section so that the third section is the rearward or posterior section.

13. A splint according to claim 12 in which the third section is a lip, shelf or ledge.

14. A splint according to claim 1 in which the second or forward portion is a forwardly inclined portion for increasing the clearance of the rearwardly located teeth whereas the rear or third section prevents substantial rearward movement of the jaw to adopt a substantially permanent position.

15. A splint according to claim 12 in which the third section stabilises or tends to stabilise the position of the jaw to or towards the usual habitual closing position.

16. A splint according to claim 1 in which the first and/or second contact section is flat, curved or a combination of different shapes.

17. An occlusal splint for the treatment of bruxism in one having opposing first and second arches of teeth in one's mouth, said occlusal splint comprising:
a first arch retentive portion and a second arch contacting portion,
said first arch retentive portion being adapted to receive incisors but no molars of said first arch of teeth, and comprising means to retain said splint in a fixed position relative to said first arch of teeth,
said second arch contacting portion comprising a tooth trough adapted to receive incisors but no molars of said second arch of teeth when said first and second arches of teeth are disposed in a habitual teeth together position in the mouth,
said tooth trough of said second arch contacting portion comprising first and second substantially planar surface sections that intersect at an angle greater than about 90° and less than about 180°, such that the incisors of said second arch of teeth are not restrained from anterior, posterior or lateral movement relative to said tooth trough, but are free to move against said first and second surface sections on relative movement of said first and second arches of teeth.

18. An occlusal splint according to claim 17, said tooth trough further comprising a third substantially planar surface section that intersects said first surface section, opposite said second surface section, at an angle greater than about 90° and less than about 180°, thereby defining a substantially U-shaped cross-section for said tooth trough.

19. A splint according to claim 3 in which the retaining means comprises at least four indentations moulded to the shape of the teeth to be received in the indentations.

20. A splint according to claim 3 in which the retaining means comprises at least six or more indentations moulded to the shape of the teeth to be received in the indentations.

21. A splint according to claim 5 in which the teeth of the upper arch are the central upper four teeth.

22. A splint according to claim 5 in which the teeth of the upper arch are the central upper six teeth.

23. A splint according to claim 7 in which the first section of the contact portion is located more forwardly of the central or intermediate portion.

24. A splint according to claim 10 in which the angle of inclination between the first section of the contact portion and the second section of the contact portion is from about 110° to about 160°.

25. A splint according to claim 10 in which the angle of inclination between the first section of the contact portion and the second section of the contact portion is from about 115° to 145°.

26. A splint according to claim 8 in which the third or rearward section prevents or minimises posterior shift and assists in moving the jaw into the normal position and remaining the jaw in this position when the device is not in use.

27. A splint according to claim 12 in which the third section is angularly inclined to the central or intermediate section.

28. A sprint according to claim 1 in which the splint is made from a single material or is made from two or more materials including a composite material or a material of a layered or laminate structure having two or more layers of different materials.

29. A splint according to claim 28 in which there is an outer tray or shell of relatively harder material and a layer of relatively softer heat softenable material located within the tray or shell.

30. An occlusal splint according to claim 17, wherein said first and second planar surface sections of said tooth trough are arranged so that on clenching together said arches of teeth, at least the incisors of said second arch of teeth are caused to move against said second surface section of said tooth trough so as to maintain a space in between opposing molars of said first and second arches of teeth so that said opposing molars are not permitted to grind against one another.

31. An occlusal splint according to claim 30, wherein said first surface section of said tooth trough is oriented so that it normally is in contact with incisors of said second arch of teeth in the habitual teeth together position, the angle of intersection between said first and second surface sections resulting in an increase in distance between said opposing molars of said first and second arches of teeth as said incisors of said second arch of teeth move forward out of contact with said first surface section and against said second surface section, while said first arch of teeth is retained in a fixed position relative to said splint.

32. An occlusal splint according to claim 17, said first and second surface sections defining a substantially V-shaped cross-section for said tooth trough.

33. An occlusal splint according to claim 17, each of said first and second surface sections of said tooth trough having a curved surface so as to define a substantially arcuate contour of said tooth trough adapted to accommodate an arcuate conformation of teeth for said second arch of teeth.

34. An occlusal splint according to claim 17, said retention means comprising a plurality of tooth-receiving pockets that are the negative complement to selected teeth of said first arch of teeth to be received and retained therein, respectively, when said splint is fitted over said first arch of teeth.

* * * * *